United States Patent
Gebauer et al.

(10) Patent No.: US 7,189,680 B2
(45) Date of Patent: Mar. 13, 2007

(54) 5-HALO-6-ARYL[1,2,4]TRIAZOLO[1,5-A]PY-RIMIDIN-7-AMINES

(75) Inventors: Olaf Gebauer, Köln (DE); Jörg Nico Greul, Leichlingen (DE); Ulrich Heinemann, Leichlingen (DE); Hans-Ludwig Elbe, Wuppertal (DE); Bernd-Wieland Krüger, Bergisch Gladbach (DE); Ralf Dunkel, Monheim (DE); Arnd Voerste, Köln (DE); Ronald Ebbert, Monheim (DE); Astrid Mauler-Machnik, Leichlingen (DE); Ulrike Wachendorff-Neumann, Neuwied (DE); Karl-Heinz Kuck, Langenfeld (DE); Yoshinori Kitagawa, Tochigi (JP)

(73) Assignee: Bayer Cropscience AG, Monheim (DE)

( * ) Notice: Subject to any disclaimer, the term of this patent is extended or adjusted under 35 U.S.C. 154(b) by 20 days.

(21) Appl. No.: 10/475,317

(22) PCT Filed: Apr. 16, 2002

(86) PCT No.: PCT/EP02/04187

§ 371 (c)(1),
(2), (4) Date: Mar. 26, 2004

(87) PCT Pub. No.: WO02/088125

PCT Pub. Date: Nov. 7, 2002

(65) Prior Publication Data

US 2004/0176398 A1 Sep. 9, 2004

(30) Foreign Application Priority Data

Apr. 27, 2001 (DE) ............................. 101 21 101

(51) Int. Cl.
*A01N 43/90* (2006.01)
*C07D 487/04* (2006.01)
*C07C 269/04* (2006.01)

(52) U.S. Cl. .................. 504/241; 544/263; 560/160; 560/161; 564/301; 564/509; 564/510

(58) Field of Classification Search ........... 514/259.31; 544/263; 560/160, 161; 564/301, 509, 510; 504/241

See application file for complete search history.

(56) References Cited

U.S. PATENT DOCUMENTS

| | | | |
|---|---|---|---|
| 3,178,467 A | 4/1965 | Gerjorich et al. | 260/456 |
| 4,408,055 A * | 10/1983 | Forster et al. | 548/125 |
| 5,593,996 A * | 1/1997 | Pees et al. | 514/259.31 |
| 5,612,345 A | 3/1997 | Becher et al. | 514/258 |
| 5,756,509 A | 5/1998 | Pees | 514/258 |
| 5,808,066 A | 9/1998 | Krummel et al. | 544/263 |
| 5,817,663 A | 10/1998 | Pees et al. | 544/263 |
| 5,854,252 A | 12/1998 | Pees et al. | 514/258 |
| 5,965,561 A | 10/1999 | Pees et al. | 514/258 |
| 6,020,338 A | 2/2000 | Pfrengle et al. | 514/258 |
| 2002/0068744 A1* | 6/2002 | Schmitt et al. | 514/259.31 |

FOREIGN PATENT DOCUMENTS

| | | |
|---|---|---|
| EP | 0 550 113 | 7/1993 |
| EP | 550113 A2 * | 7/1993 |
| FR | 1592328 * | 5/1970 |
| WO | 98/46607 | 10/1998 |
| WO | 98/46608 | 10/1998 |
| WO | WO 02/02563 A2 * | 1/2002 |

OTHER PUBLICATIONS

Davidson, E.B. et al, JOC, 27, 2267-2269, 1962.*
Donald A. Cooper, Future Synthetic Drugs of Abuse Drug Enforcement Administration McLean, Virginia [retrieved on Mar. 24, 2006]. Retrieved from the Internet <http://www.erowid.org/library/books_online/future_synthetic/future_synthetic.shtml#Phencyclidine>.*
Reddy, K.R. et al, Synthesis, 1995, 929-930.*
Bouzard, D. et al, J. Med. Chem., 35, 518-525, 1992.*
Repke, D.B. et al, J. Het. Chem., 14, 71-74, 1977.*
Atto, S. Y. et al: Free radical substitution in aliphatic compounds. Part 36. The chlorination of 1,1,1-trifluoro-2- methylbutane Journal of Fluorine Chemistry, 21(3), 397-400 Coden: JFLCAR; ISSN: 0022-1139, 1982, XP002299103.
T. Moriwake et al.: "Synthesis of chiral (8S)-7-aza-1,3(E),9-decatriene system from natural alpha amino acids and its intramolecular Diels-alder-reaction directed toward chiral trans-hydroisoquinolones" J. Org. Chem. Bd. 54, 1989, Seiten 4114-4120 XP002299104.
G. Crisp et al.: "Palladium-catalyzed Heck couplings of L-vinylglycine derivatives with vinyl and aryl halides and triflates" Tetrahedron, Bd. 48, Nr. 17, 1992, Seiten 3451-3556, XP002299105 Saure Hydrolyse der Verbindung 4 (seihe Seiten 3548-3459).
R. Dannley et al.: "Use of sodium hydride in alkylation or urethans" J. Org. Chem., Bd. 22, Nr. 3, 1957, Seiten 268-270, XP002299106 * Tabelle 1 *.

* cited by examiner

Primary Examiner—Mark L. Berch
Assistant Examiner—Susanna Moore
(74) Attorney, Agent, or Firm—Richard E. L. Henderson

(57) ABSTRACT

The invention relates to novel triazolopyrimidines of the formula (I)

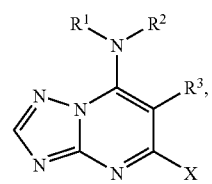

in which $R^1$, $R^2$, $R^3$ and X have the meanings given in the disclosure, and acid addition salts thereof, to a plurality of processes for preparing these novel substances, and to their use for controlling unwanted microorganisms.

The invention further relates to novel amines and carbamates of the formulae indicated in the description and to processes for preparing these intermediates.

7 Claims, No Drawings

5-HALO-6-ARYL[1,2,4]TRIAZOLO[1,5-A]PYRIMIDIN-7-AMINES

The present invention relates to novel triazolopyrimidines, to a plurality of processes for their preparation and to their use for controlling unwanted microorganisms.

It is already known that certain triazolopyrimidines have fungicidal properties (cf. EP-A 0 550 113, WO 94-20 501, EP-A 0 613 900, U.S. Pat. No. 5,612,345, EP-A 0 834 513, WO 98-46 607 and WO 98-46 608). The activity of these substances is good; however, at low application rates, it is sometimes unsatisfactory.

This invention, accordingly, provides novel triazolopyrimidines of the formula

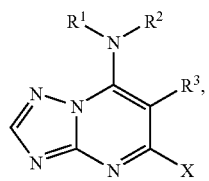
(I)

in which
- $R^1$ represents hydroxyl, amino, alkylcarbonylamino, N-alkyl-N-alkoxycarbonylamino, alkoxycarbonylamino, represents optionally substituted alkoxy, optionally substituted alkenyloxy, optionally substituted alkinyloxy, optionally substituted cycloalkyloxy, optionally substituted alkylamino, optionally substituted dialkylamino, optionally substituted alkenylamino, optionally substituted alkinylamino, optionally substituted cycloalkylamino, optionally substituted N-cycloalkyl-N-alkylamino, optionally substituted alkylideneamino, optionally substituted heterocyclyloxy or a radical of the formula —S—$R^4$, in which
  - $R^4$ represents optionally substituted alkyl, optionally substituted alkenyl, optionally substituted alkinyl or optionally substituted cycloalkyl,
- $R^2$ represents hydrogen, optionally substituted alkyl, optionally substituted alkenyl, optionally substituted alkinyl, or optionally substituted cycloalkyl,
- $R^3$ represents optionally substituted aryl, and
- X represents halogen, and also acid addition salts of those compounds of the formula (I) in which
- $R^1$ represents amino.

Depending on substitution pattern the compounds of the invention may be present where appropriate as mixtures of different possible isomeric forms, particularly of stereoisomers such as, for example, E and Z isomers, threo and erythro isomers, and also optical isomers, or even, where appropriate, of tautomers. Where $R^3$ is substituted differently on both atoms adjacent to the bond site, the compounds in question may be present in a particular form of stereoisomerism, namely as atropisomers.

Furthermore, it has been found that triazolopyrimidines of the formula (I) can be prepared by a) reacting dihalogeno-triazolopyrimidines of the formula

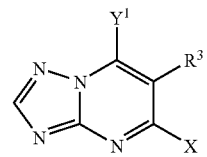
(II)

in which
$R^3$ and X have the meanings given above and
$Y^1$ represents halogen with amines of the formula

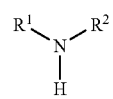
(III)

in which
$R^1$ and $R^2$ have the meanings given above,
if appropriate in the presence of a diluent and if appropriate in the presence of an acid acceptor,
or b) reacting triazolopyrimidines of the formula

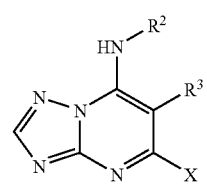
(IV)

in which
$R^2$, $R^3$ and X have the meanings given above
with sulphenyl halides of the-formula $$Y2\text{-}S\text{—}R4 \quad (V)$$

in which
$R^4$ has the meanings given above and
$Y^2$ represents halogen,
if appropriate in the presence of a diluent and if appropriate in the presence of an acid acceptor,
and optionally adding an acid onto the resulting compounds of the formula (I) in which
$R^1$ represents amino.

Finally, it has been found that the novel triazolopyrimidines of the formula (I) and their acid addition salts are highly suitable for controlling unwanted microorganisms. In particular, they have strong fungicidal activity and can be used both in crop protection and in the protection of materials.

Surprisingly, the triazolopyrimidines of the formula (I) according to the invention have considerably better microbicidal activity than the constitutionally most similar prior-art substances of the same direction of action.

The formula (I) provides a general definition of the triazolopyrimidines according to the invention. Preference is given to those substances of the formula (I) in which
$R^1$ represents hydroxyl, amino, alkylcarbonylamino having 1 to 6 carbon atoms in the alkyl group, N-alkyl-N-alkoxycarbonyl-amino having 1 to 6 carbon atoms in the alkyl group and 1 to 6 carbon atoms in the alkoxy group, or represents alkoxycarbonyl-amino having 1 to 6 carbon atoms in the alkoxy group, or $R^1$ represents alkoxy having 1 to 7 carbon atoms which is optionally substituted by halogen, cycloalkyl, cyano, phenyl, phenoxy, heterocyclyl and/or heterocyclyloxy, or $R^1$ represents alkenyloxy having 2 to 6 carbon atoms which is optionally substituted by halogen, cycloalkyl, cyano, phenyl and/or heterocyclyl, represents alkinyloxy having 2 to 6 carbon atoms which is optionally substituted by halogen, cycloalkyl, cyano, phenyl and/or heterocyclyl, represents cycloalkyloxy having 3 to 7 carbon atoms which is optionally substituted by halogen, cycloalkyl, cyano, phenyl and/or heterocyclyl, represents alkylamino having 1 to 7 carbon atoms which is optionally substituted by halogen, cycloalkyl, cyano, hydroxyl, phenyl and/or heterocyclyl, or $R^1$ represents dialkylamino having 1 to 7 carbon atoms in each of the alkyl radicals which is optionally substituted by halogen, cycloalkyl, cyano, phenyl and/or heterocyclyl, represents alkenylamino having 2 to 6 carbon atoms which is optionally substituted by halogen, cycloalkyl, cyano, phenyl and/or heterocyclyl, represents alkinylamino having 2 to 6 carbon atoms which is optionally substituted by halogen, cycloalkyl, cyano, phenyl and/or heterocyclyl, represents cycloalkylamino having 3 to 7 carbon atoms which is optionally substituted by halogen, alkyl, cycloalkyl, cyano, phenyl and/or heterocyclyl, represents N-cycloalkyl-N-alkyl-amino having 3 to 7 carbon atoms in the cycloalkyl moiety and 1 to 7 carbon atoms in the alkyl moiety which is optionally substituted by halogen, cycloalkyl, cyano, phenyl and/or heterocyclyl, represents alkylideneamino having 1 to 6 carbon atoms which is optionally substituted by halogen, cycloalkyl, cyano, phenyl and/or heterocyclyl, represents optionally substituted heterocyclyloxy having 5 or 6 ring members and 1 or 2 heteroatoms in the heterocycle or represents —$SR^4$, in which $R^4$ represents alkyl having 1 to 6 carbon atoms which is optionally substituted by halogen, cycloalkyl, cyano, phenyl and/or heterocyclyl, represents alkenyl having 2 to 6 carbon atoms which is optionally substituted by halogen, cycloalkyl, cyano, phenyl and/or heterocyclyl, represents alkinyl having 2 to 6 carbon atoms which is optionally substituted by halogen, cycloalkyl, cyano, phenyl and/or heterocyclyl or represents cycloalkyl having 3 to 7 carbon atoms which is optionally substituted by halogen, cycloalkyl, cyano, phenyl and/or heterocyclyl, where the heterocyclyl radicals mentioned above may be mono- to trisubstituted by identical or different substituents from the group consisting of halogen, alkyl having 1 to 4 carbon atoms, halogenoalkyl having 1 or 2 carbon atoms and 1 to 5 halogen atoms, alkoxy having 1 to 4 carbon atoms, alkylthio having 1 to 4 carbon atoms, halogenoalkoxy having 1 or 2 carbon atoms and 1 to 5 halogen atoms, halogenoalkylthio having 1 or 2 carbon atoms and 1 to 5 halogen atoms and/or phenyl, and where the phenyl radicals mentioned above may be mono- to trisubstituted by identical or different substituents from the group consisting of halogen, cyano, nitro, amino, hydroxyl, formyl, carboxyl, carbamoyl, thiocarbamoyl;

in each case straight-chain or branched alkyl, alkoxy, alkylthio, alkylsulphinyl or alkylsulphonyl having in each case 1 to 6 carbon atoms; in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 13 identical or different halogen atoms;

in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties;

cycloalkyl having 3 to 6 carbon atoms, or may be monosubstituted by alkylene having 3 or 4 carbon atoms or dioxyalkylene having 1 or 2 carbon atoms, where these radicals are doubly attached in the ortho position and may be mono- to tetrasubstituted by identical or different substituents from the group consisting of halogen, alkyl having 1 to 4 carbon atoms and/or halogenoalkyl having 1 to 4 carbon atoms and 1 to 9 identical or different halogen atoms, $R^2$ represents hydrogen, represents alkyl having 1 to 6 carbon atoms which is optionally substituted by halogen, alkoxy having 1 or 2 carbon atoms, alkylthio having 1 or 2 carbon atoms, oxo, hydroximino, alkoximino having 1 or 2 carbon atoms, cycloalkyl having 3 to 7 carbon atoms, cycloalkyl having 3 to 6 carbon atoms which is substituted by halogen, and/or heterocyclyl, represents alkenyl having 2 to 4 carbon atoms which is optionally substituted by halogen and/or cycloalkyl having 3 to 6 carbon atoms, represents alkinyl having 2 to 4 carbon atoms which is optionally substituted by halogen and/or cycloalkyl having 3 to 6 carbon atoms or represents cycloalkyl having 3 to 8 carbon atoms which is optionally substituted by halogen and/or cycloalkyl having 3 to 6 carbon atoms, $R^3$ represents phenyl which may be mono- to pentasubstituted by identical or different substituents from the group consisting of halogen, cyano, nitro, amino, hydroxyl, formyl, carboxyl, carbamoyl, thiocarbamoyl;

in each case straight-chain or branched alkyl, alkoxy, alkylthio, alkylsulphinyl or alkylsulphonyl having in each case 1 to 6 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 13 identical or different halogen atoms;

in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties;

cycloalkyl having 3 to 6 carbon atoms, or may be monosubstituted by alkylene having 3 or 4 carbon atoms or dioxyalkylene having 1 or 2 carbon atoms, where these radicals are doubly attached in the ortho position and may be mono- to tetrasubstituted by identical or different substituents from the group consisting of halogen, alkyl having 1 to 4 carbon atoms and/or halogenoalkyl having 1 to 4 carbon atoms and 1 to 9 identical or different halogen atoms, and X represents fluorine, chlorine or bromine.

Particular preference is given to triazolopyrimidines of the formula (I) in which $R^1$ represents hydroxyl, amino, alkylcarbonylamino having 1 to 4 carbon atoms in the alkyl group, N-alkyl-N-alkoxycarbonyl-amino having 1 to 4 carbon atoms in the alkyl group and 1 to 4 carbon atoms in the alkoxy group, or represents alkoxycarbonyl-amino having 1 to 4 carbon atoms in the alkoxy group, or $R^1$ represents methoxy, ethoxy, n- or isopropoxy, n-, iso-, s- or t-butoxy, allyloxy, butenyloxy, propargyloxy, cyclopropyloxy, cyclobutyloxy, cyclopentyloxy, cyclohexyloxy, hexahydropyranyloxy, difluoromethoxy, trifluoromethoxy, difluorochloromethoxy, trifluoroethoxy or represents a radical of the formula O—(CH$_2$)$_n$—R$^5$ in which n represents 1 or 2 and $R^5$ represents optionally substituted phenyl, optionally substituted pyridyl, optionally substituted pyridyloxy, optionally substituted thiazolyl, tetrahydrofuranyl or morpholinyl, or $R^1$ represents methylamino, ethylamino, n-propylamino, isopropylamino, n-, iso-, s- or t-butylamino, 1-ethylpropylamino, 3-methylbutylamino, 2-hydroxyethylamino, 2-hydroxy-2-methyl-propylamino, 2,2,2-trifluoroethylamino, 2,2,3,3-tetrafluoropropylamino, 2-cyano-ethylamino, 1-cyclopropyl-ethylamino, cyclopropyl-methylamino, cyclopentyl-methylamino, cyclohexyl-methylamino, dimethylamino, allylamino, 2-methyl-prop-1-enylamino, propargylamino, cyclopropylamino, cyclobutylamino, cyclopentylamino, cyclohexylamino, 1-methyl-cyclohexylamino, methylideneamino, 1-methyl-ethylideneamino, 2,2,2-trifluoro-1-methyl-ethylidene-amino, dichlorocyclopropyl-methylamino or represents —S—R$^4$, in which $R^4$ represents methyl, ethyl, n- or isopropyl, difluoromethyl, difluorochloromethyl, dichlorofluoromethyl or trifluoromethyl, where the thiazolyl and pyridyl radicals mentioned above may in each case be substituted, in the case of thiazolyl mono- or disubstituted and in the case of pyridyl mono- to trisubstituted, by identical or different substituents from the group consisting of fluorine, chlorine, bromine, methyl, ethyl, n- or isopropyl, n- iso-, s- or t-butyl, methoxy, ethoxy, n- or isopropoxy, n-, iso-, s- or t-butoxy, methylthio, ethylthio, n- or isopropylthio, difluoromethoxy, trifluoromethoxy, difluorochloromethoxy, trifluoroethoxy, difluoromethylthio, difluorochloromethylthio, dichlorofluoromethylthio, trifluoromethylthio and phenyl, and the phenyl radicals mentioned above may be mono- to trisubstituted by identical or different substituents from the group consisting of fluorine, chlorine, bromine, cyano, nitro, amino, hydroxyl, formyl, carboxyl, carbamoyl, thiocarbamoyl, methyl, ethyl, n- or i-propyl, n-, iso-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl, ethoximinoethyl, cyclopropyl, cyclobutyl, cyclopentyl or cyclohexyl, or may be monosubstituted by propene-1,3-diyl, methylenedioxy or ethylenedioxy, where these radicals are doubly attached in the ortho-position and may be mono- to tetrasubstituted by identical or different substituents from the group consisting of fluorine, chlorine, methyl, ethyl, n-propyl, isopropyl and/or trifluoromethyl, $R^2$ represents hydrogen, methyl, ethyl, n- or isopropyl, n-, iso-, s- or t-butyl, allyl, propargyl, 2,2,2-trifluoroethyl, 1-(1,1,1-trifluoromethyl)ethyl, cyclopropylmethyl, cyclobutylmethyl, cyclopentylmethyl, cyclohexylmethyl, cyclopropyl, cyclobutyl, cyclopentyl, cyclohexyl, cycloheptyl, dichlorocyclopropyl-methyl, tetrahydrofuryl-methyl, 2-morpholinoethyl, or represents methoxy-methyl, 2-methoxy-ethyl, methylthio-methyl, 2-methylthio-ethyl, or a radical of the formula

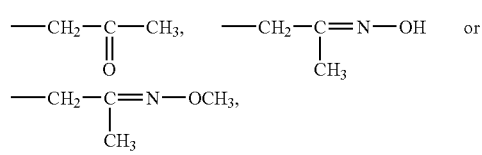

$R^3$ represents phenyl which may be mono- to pentasubstituted by identical or different substituents from the group consisting of fluorine, chlorine, bromine, cyano, nitro, formyl, methyl, ethyl, n- or isopropyl, n-, iso-, s- or t-butyl, allyl, propargyl, methoxy, ethoxy, n- or isopropoxy, methylthio, ethylthio, n- or isopropylthio, methylsulphinyl, ethylsulphinyl, methylsulphonyl, ethylsulphonyl, allyloxy, propargyloxy, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, trichloroethinyloxy, trifluoroethinyloxy, chloroallyloxy, iodopropargyloxy, methylamino, ethylamino, n- or i-propylamino, dimethylamino, diethylamino, acetyl, propionyl, acetyloxy, methoxycarbonyl, ethoxycarbonyl, hydroximinomethyl, hydroximinoethyl, methoximinomethyl, ethoximinomethyl, methoximinoethyl, ethoximinoethyl, cyclopropyl, cyclobutyl, cyclopentyl and cyclohexyl, or may be monosubstituted by propane-1,3-diyl, methylenedioxy or ethylenedioxy, where these radicals are doubly attached in the ortho-position and may be mono- to tetrasubstituted by identical or different substituents from the group consisting of fluorine, chlorine, methyl, ethyl, n-propyl, isopropyl and trifluoromethyl, and X represents fluorine or chlorine Very particular preference is given to those compounds of the formula (I) in which $R^1$, $R^2$ and X have the meanings given above and $R^3$ represents 2,4-disubstituted, 2,6-disubstituted or 2,4,6-trisubstituted phenyl.

The radical definitions mentioned above can be combined with one another as desired. Moreover, individual meanings may not apply.

Preferred compounds according to the invention are also addition products of acids and those triazolopyrimidines of the formula (I), in which $R^1$ represents amino and $R^2$, $R^3$ and X have those meanings which were stated as preferred for these radicals.

The acids which can be added on include preferably hydrohalic acids, such as hydrochloric acid and hydrobromic acid, for example, especially hydrochloric acid, and also phosphoric acid, nitric acid, monofunctional and bifunctional carboxylic acids and hydroxycarboxylic acids, such as acetic acid, maleic acid, succinic acid, fumaric acid, tartaric acid, citric acid, salicylic acid, sorbic acid and lactic acid, for example, and also sulphonic acids, such as p-toluenesulphonic acid, 1,5-naphthalenedisulphonic acid, saccharin and thiosaccharin, for example.

Using 5,7-dichloro-6-(2,4,6-trifluorophenyl)-[1,2,4]-triazolo[1,5-a]-pyrimidine and N,N-dimethylhydrazine as starting materials, the course of the process (a) according to the invention can be illustrated by the formula scheme below.

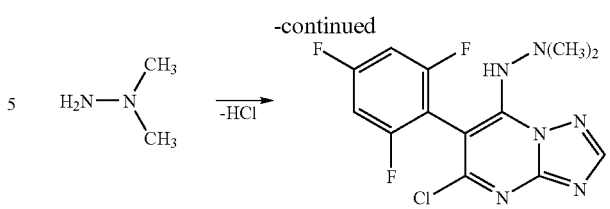

Using 5-chloro-N-[(1S)-2,2,2-trifluoro-1-methyl-ethyl]-6-(2,4,6-trifluorophenyl)-[1,2,4]-triazolo-[1,5-a]pyrimidin-7-amine and dichlorofluoromethane-sulphenyl chloride as starting materials, the course of the process (b) according to the invention can be illustrated by the formula scheme below.

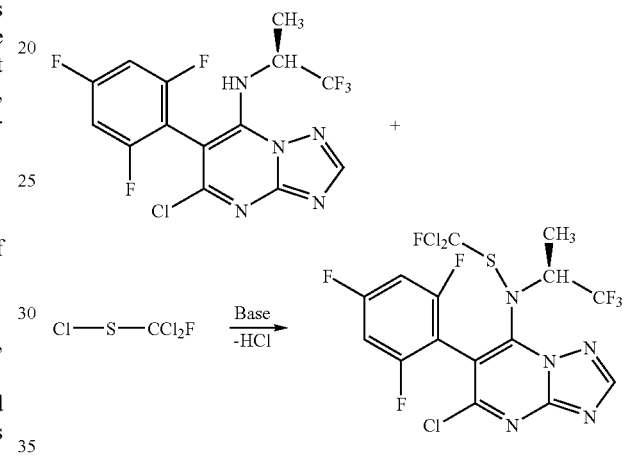

The formula (II) provides a general definition of the dihalogeno-triazolo-pyrimidines required as starting materials for carrying out the process (a) according to the invention. In this formula, $R^3$ and X preferably have those meanings which have already been mentioned in connection with the description of the substances of the formula (I) according to the invention as being preferred for these radicals. $Y^1$ preferably represents fluorine, chlorine or bromine, particularly preferably fluorine or chlorine.

The dihalogeno-triazolopyrimidines of the formula (II) known or can be prepared according to known methods (cf. U.S. Pat. No. 5,808,066, U.S. Pat. No. 5,612,345 and WO 94-20 501).

The formula (III) provides a general definition of the amines furthermore required as starting materials for carrying out the process (a) according to the invention. In this formula, $R^1$ and $R^2$ preferably have those meanings which have already been mentioned in connection with the description of the compounds of the formula (I) according to the invention as being preferred for $R^1$ and $R^2$.

Some of the amines of the formula (III) are known.

Novel amines are those of the formula

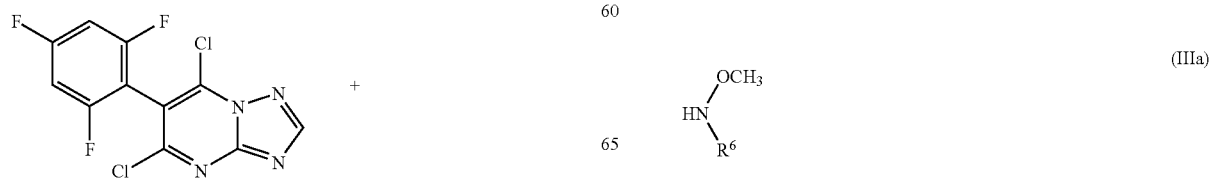

in which
R⁶ represents isobutyl, 2-methoxyethyl or represents

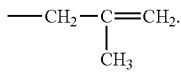

The amines of the formula (IIIa) can be prepared by
c) in a first stage reacting ethyl N-methoxycarbamate of the formula

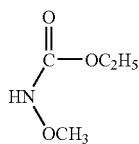

(VI)

with halogen compounds of the formula

R⁶—X¹  (VII)

in which
R⁶ has the meanings given above and
X¹ represents bromine or iodine
in the presence of a base and in the presence of a diluent and in a second stage reacting the resulting carbamates of the formula

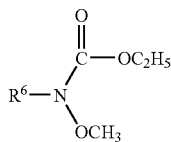

(VIII)

in which
R⁶ has the meanings given above
with potassium hydroxide in the presence of ethanol and water.
Novel amines are also those of the formula

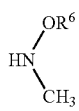

(IIIb)

in which
R⁶ has the meanings given above.
The amines of the formula (IIIb) can be prepared by
d) in a first stage reacting ethyl N-hydroxy-N-methylcarbamate of the formula

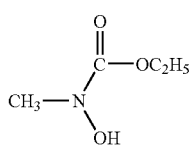

(IX)

with halogen compounds of the formula

R⁶—X¹  (VII)

in which
R⁶ and X¹ have the meanings given above
in the presence of a base and in the presence of a diluent and in a second stage reacting the resulting carbamates of the formula

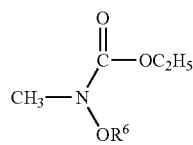

(X)

in which
R⁶ has the meanings given above
with potassium hydroxide in the presence of ethanol and water.
Also novel are trifluoroisopropylamines of the formula

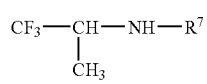

(IIIc)

in which
R⁷ represents methyl, ethyl or propyl.
The trifluoroisopropylamines of the formula (IIIc) can be prepared by
e) in a first stage reacting ethyl N-trifluoroisopropylcarbamate of the formula

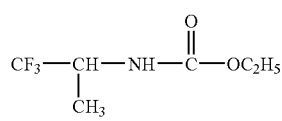

(XI)

with halogen compounds of the formula

R⁷—X¹  (XII)

in which
R⁷ and X¹ have the meanings given above
in the presence of a base and in the presence of a diluent and in a second stage reacting the resulting carbamates of the formula

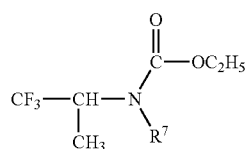

(XIII)

in which
R⁷ has the meanings given above
with potassium hydroxide in the presence of ethanol and water.
Also novel, finally, is the 3-trifluoro-methyl-3-aminopropene of the formula (III-4), obtainable by f) reacting the carbamate of the formula

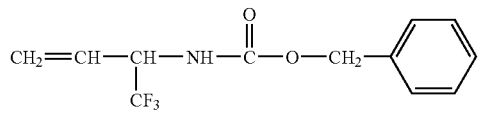

(XIV)

with aqueous hydrochloric acid.

The compounds of the formulae (VI), (VII), (IX), (XI), (XII) and (XIV) required as starting compounds for carrying out the processes (c)–(f) according to the invention are known or can be prepared by known methods.

Organic and inorganic acid acceptors suitable for carrying out the first stage of the processes (c), (d) and (e) according to the invention are in each case all those which are customary for such reactions.

With preference it is possible to use alkaline earth metal or alkali metal hydrides, hydroxides, amides, alkoxides, acetates, carbonates or bicarbonates, such as sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium bicarbonate and sodium bicarbonate, and also ammonium compounds, such as ammonium hydroxide, ammonium acetate and ammonium carbonate. Organic bases that may be mentioned include the following: tertiary amines, such as trimethylamine, triethylamine, tributylamine, N,N-dimethylaniline, N,N-dimethyl-benzylamine, pyridine, N-methylpiperidine, N-methylmorpholine, N,N-dimethylamino-pyridine, diazabicyclooctane (DABCO), diazabicyclononene (DBN) or diazabicycloundecene (DBU).

Suitable diluents for carrying out the first stage of the processes (c), (d) and (e) according to the invention include in each case all customary inert inorganic solvents. With preference it is possible to use ethers, such as diethyl ether, dioxane, tetrahydrofuran, 1,2-dimethoxyethane, 1,2-diethoxyethane or anisole; amides, such as N,N-dimethylformamide, N,N-dimethylacetamide, N-methylformanilide or N-methylpyrrolidone; sulphones, such as sulpholane; alcohols such as methanol, ethanol, isopropanol, tert-butanol, n-butanol.

The reaction temperatures when carrying out the first stage of the processes (c), (d) and (e) according to the invention may in each case be varied within a relatively wide range. It is normal to work at temperatures between 0° C. and 150° C., preferably between 10° C. and 100° C.

When carrying out the first stage of the processes (c), (d) and (e) according to the invention it is normal to operate in each case under atmospheric pressure. It is also possible, however, to operate under increased pressure or, where no low-boiling components participate in the reaction, under reduced pressure.

When carrying out the first stage of the processes (c), (d) and (e) according to the invention, generally from 0.5 to 15 mol, preferably from 1 to 5 mol, of halogen compound of the formula (VII) are used per mole of ethyl N-methoxycarbamate of the formula (VI), and generally from 0.5 to 15 mol, preferably from 1 to 5 mol, of halogen compound of the formula (VII) are used per mole of ethyl N-hydroxy-N-methylcarbamate of the formula (IX), or generally from 0.5 to 15 mol, preferably from 1 to 5 mol, of halogen compound of the formula (XII) are used per mole of ethyl N-trifluoroisopropylcarbamate of the formula (XI).

Working up is carried out in each case by customary methods, for example by extraction and subsequent drying or by precipitation with subsequent filtration and drying. Any impurities still present can be removed in accordance with customary methods.

The compounds of the formulae (VIII), (X) and (XIII) obtained as intermediates when carrying out the first stage of processes (c), (d) and (e) according to the invention are novel.

When carrying out the second stage of the processes (c), (d), and (e) according to the invention it is also possible to vary the reaction temperatures in each case within a relatively wide range. It is normal to work at temperatures between 0° C. and 100° C., preferably between 10° C. and 80° C.

When carrying out the second stage of the processes (c), (d) and (e) it is normal to operate in each case under atmospheric pressure. It is, however, again possible to operate in each case under increased pressure or, where the products to be isolated do not have very low boiling points, under reduced pressure.

When carrying out the second stage of the processes (c), (d) and (e) according to the invention in each case up to 10 mol of potassium hydroxide are used per mole of a compound of the formula (VIII), (X) or (XIII). Working up is carried out in accordance with customary methods. It involves isolating the amines in the form of their salts, appropriately in general by adding acid, preferably aqueous hydrochloric acid.

When carrying out the process (f) according to the invention it is likewise possible to vary the reaction temperatures within a relatively wide range. It is normal to operate at temperatures between 10° C. and 150° C., preferably at reflux temperature.

It is normal to operate under atmospheric pressure when carrying out the process (f) according to the invention. It is, however, also possible to operate under increased pressure.

When carrying out the process (f) according to the invention an excess, preferably up to 10 mol, of aqueous hydrochloric acid are used per mole of carbamate of the formula (XIV). Working up is again carried out in accordance with customary methods.

The formula (IV) provides a general definition of the triazolopyrimidines required as starting materials for carrying put the process (b) according to the invention. In this formula, $R^2$, $R^3$ and X preferably have those meanings which have already been mentioned in connection with the description of the substances of the formula (I) according to the invention as being preferred for these radicals.

The triazolopyrimidines of the formula (IV) are substances which can be prepared in a manner similar to process (a) according to the invention.

The formula (V) provides a general definition of the sulphenyl halides furthermore required as starting materials for carrying out the process (b) according to the invention. In this formula, $R^4$ preferably has those meanings which have already been mentioned in connection with the description of the compounds of the formula (I) according to the invention as being preferred for this radical.

$Y^2$ preferably represents fluorine, chlorine or bromine, particularly preferably chlorine.

The sulphenyl halides of the formula (V) are known or can be prepared by known methods.

Suitable diluents for carrying out the process (a) according to the invention are all customary inert organic solvents. Preference is given to using aliphatic, alicyclic or aromatic hydrocarbons, such as hexane, heptane, cyclohexane or toluene; halogenated hydrocarbons, such as chlorobenzene, dichlorobenzene, dichloromethane, chloroform, carbon tetrachloride, dichloroethane or trichloroethane; ethers, such as diethyl ether, diisopropyl ether, methyl tert-butyl ether, dioxane, tetrahydrofuran, 1,2-dimethoxyethane or 1,2-diethoxyethane; amides, such as N,N-dimethylformamide, N,N-dimethylacetamide or N-methylpyrrolidone; esters, such as methyl acetate or ethyl acetate; sulphoxides, such as dimethyl sulphoxide; sulphones, such as sulpholane.

Suitable acid acceptors for carrying out the process (a) according to the invention are all acid binders which are customary for such reactions. Preference is given to using tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process (a) according to the invention, the reaction temperatures may be varied within a relatively wide range. In general, the process is carried out at temperatures between 0° C. and 150° C., preferably at temperatures between 0° C. and 80° C.

Both the process (a) and the process (b) according to the invention are generally carried out under atmospheric pressure. However, it is also possible to operate under elevated or reduced pressure, in general between 0.1 and 10 bar.

When carrying out the process (a) according to the invention, in general from 0.5 to 10 mol, preferably from 0.8 to 2 mol, of the amine of the formula (III) are employed per mole of dihalogeno-triazolo-pyrimidine of the formula (II). Work-up is carried out by customary methods.

Suitable diluents for carrying out the process (b) according to the invention are all customary inert organic solvents. Preference is given to using ethers, such as diethyl ether, dioxane, tetrahydrofuran, 1,2-dimethoxyethane, 1,2-diethoxyethane or anisole; amides, such as N,N-dimethylformamide, N,N-dimethylacetamide, N-methylformanilide or N-methylpyrrolidone; sulphones, such as sulpholane.

Suitable acid acceptors for carrying out- the process (b) according to the invention are all inorganic and organic bases which are customary for such reactions. Preference is given to using alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium bicarbonate and sodium bicarbonate, and furthermore ammonium compounds, such as ammonium hydroxide, ammonium acetate and ammonium carbonate.

When carrying out the process (b) according to the invention, the reaction temperatures can also be varied within a relatively wide range. In general, the process is carried out at temperatures between −40° C. and +120° C., preferably between −20° C. and +50° C.

When carrying out the process (b) according to the invention, in general from 1 to 15 mol, preferably from 1 to 8 mol, of sulphenyl halide of the formula (V) are employed per mole of triazolopyrimidine of the formula (IV). Work-up is carried out by customary methods.

Suitable acids for preparing acid addition salts of triazolopyrimidines of the formula (I) are preferably those acids already stated as being preferred acids in connection with the description of the acid addition salts according to the invention.

The acid addition salts of the compounds of the formula (I) may be obtained in a simple way in accordance with customary salt formation methods, for example by dissolving a compound of the formula (I) in a suitable inert solvent and adding the acid, e.g. hydrochloric acid, and may be isolated in a known way, for example by filtration, and may where appropriate be purified by washing with an inert organic solvent.

The substances according to the invention have potent microbicidal activity and can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacteria diseases which come under the generic names listed above may be mentioned as examples, but not by way of limitation:

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora;*

*Pythium* species, such as, for example, *Pythium ultimum;*

*Phytophthora* species, such as, for example, *Phytophthora infestans;*

*Pseudoperonospora* species, such as, for example, *Pseudoperonospora humuli* or *Pseudoperonospora cubensis;*

*Plasmopara* species, such as, for example, *Plasmopara viticola;*

*Bremia* species, such as, for example, *Bremia lactucae;*

*Peronospora* species, such as, for example, *Peronospora pisi* or *P. brassicae;*

*Erysiphe* species, such as, for example, *Erysiphe graminis;*

*Sphaerotheca* species, such as, for example, *Sphaerotheca fuliginea;*

*Podosphaera* species, such as, for example, *Podosphaera leucotricha;*

*Venturia* species, such as, for example, *Venturia inaequalis;*

*Pyrenophora* species, such as, for example, *Pyrenophora teres* or *P. graminea* (conidia form: Drechslera, syn: Helminthosporium);

*Cochliobolus* species, such as, for example, *Cochliobolus sativus* (conidia form: Drechslera, syn: Helminthosporium);

*Uromyces* species, such as, for example, *Uromyces appendiculatus;*

*Puccinia* species, such as, for example, *Puccinia recondita;*

*Sclerotinia* species, such as, for example, *Sclerotinia sclerotiorum;*

*Tilletia* species, such as, for example, *Tilletia caries;*

*Ustilago* species, such as, for example, *Ustilago nuda* or *Ustilago avenae;*

*Pellicularia* species, such as, for example, *Pellicularia sasakii*;

*Pyricularia* species, such as, for example, *Pyricularia oryzae*;

*Fusarium* species, such as, for example, *Fusarium culmorum*;

*Botrytis* species, such as, for example, *Botrytis cinerea*;

*Septoria* species, such as, for example, *Septoria nodorum*;

*Leptosphaeria* species, such as, for example, *Leptosphaeria nodorum*;

*Cercospora* species, such as, for example, *Cercospora canescens*;

*Alternaria* species, such as, for example, *Alternaria brassicae*; and

*Pseudocercosporella* species, such as, for example, *Pseudocercosporella herpotrichoides*.

The active compounds according to the invention also have very good fortifying action in plants. Accordingly, they can be used for mobilizing the defences of the plant against attack by undesirable microorganisms.

In the present context, plant-fortifying (resistance-inducing) substances are to be understood as meaning those substances which are capable of stimulating the defence system of plants such that, when the treated plants are subsequently inoculated with undesirable microorganisms, they show substantial resistance against these microorganisms.

In the present case, undesirable microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention are also suitable for increasing the yield of crops. In addition, they show reduced toxicity and are well tolerated by plants.

At certain concentrations and application rates, the active compounds according to the invention can also be used as herbicides, for influencing plant growth and for controlling animal pests. They can also be used as intermediates and precursors for the synthesis of further active compounds.

The active compounds according to the invention can be used to treat all plants and parts of plants. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and the parts of plants with the active compounds according to the invention is carried out directly or by action on their surroundings, habitat or storage space, according to customary treatment methods, for example by dipping, spraying, evaporating, atomizing, broadcasting, spreading-on and, in the case of propagation material, in particular in the case of seeds, furthermore by one- or multi-layer coating.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes), and against slime organisms and algae.

Microorganisms of the following genera may be mentioned as examples:

Alternaria, such as *Alternaria tenuis*,

Aspergillus, such as *Aspergillus niger*,

Chaetomium, such as *Chaetomium globosum*,

Coniophora, such as *Coniophora puetana*,

Lentinus, such as *Lentinus tigrinus*,

Penicillium, such as *Penicillium glaucum*,

Polyporus, such as *Polyporus versicolor*,

Aureobasidium, such as *Aureobasidium pullulans*,

Sclerophoma, such as *Sclerophoma pityophila*,

Trichoderma, such as *Trichoderma viride*,

Escherichia, such as *Escherichia coli*,

Pseudomonas, such as *Pseudomonas aeruginosa*, and

Staphylococcus, such as *Staphylococcus aureus*.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous. extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing components are the following:

Fungicides:

aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, carpropamide, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluorornide, fluquinconazole, flurprimidol, flusilazole, flusulphamide, flutolanil, flutriafol, folpet, fosetyl-aluminium, fosetyl-sodium, fthalide, fuberidazole, furalaxyl, furametpyr, furcarbonil, furconazole, furconazole-cis, furrnecyclox, fenhexamide, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, iprovalicarb kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulphocarb, methfuroxam, metiram, metomeclam, metsulphovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur, quinconazole, quintozene (PCNB), quinoxyfen, sulphur and sulphur preparations, spiroxamines, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, 1-(2,4-dichlorophenyl)-2-(1H-1,2,4-triazol-1-yl)-ethanone O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,6-dichloro-5-(methylthio)-4-pyrimidinyl-thiocyanate,
2,6-dichloro-N-(4-trifluoromethylbenzyl)-benzamide, 2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl)-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine-hydrochloride,
ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl)-N'-methoxymethanimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
4-[(3,4-dimethoxyphenyl)-3-(4-fluorophenyl)-acryloyl]-morpholine.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben,
cadusafos, carbaryl, carbofuran, carbophenothion, carbosulphan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cisresmethrin, cispermethrin, clocythrin, cloethocarb, clofentezine, clothianidine, cyanophos, cycloprene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, dicofol, diflubenzuron, dimethoat, dimethylvinphos, diofenolan, disulphoton, docusat-sodium, dofenapyn,
eflusilanate, emamectin, empenthrin, endosulphan, Entomopfthora spp., esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, indoxacarb, isazofos, isofenphos, isoxathion, ivermectin,
nuclear polyhedrosis viruses,
lambda-cyhalothrin, lufenuron,
malathion, mecarbam, metaldehyde, methamidophos, *Metharhizium anisopliae, Metharhizium flavoviride*, methidathion, methiocarb, methoprene, methomyl, methoxyfenozide, metolcarb, metoxadiazone, mevinphos, milbemectin, milbemycin, monocrotophos,
naled, nitenpyram, nithiazine, novaluron,
omethoate, oxamyl, oxydemethon M,
*Paecilomyces fumosoroseus*, parathion A, parathion M, permethrin, phenthoate, phorat, phosalone, phosmet, phosphamidon, phoxim, pirimicarb, pirimiphos A, pirimiphos M, profenofos, promecarb, propargite, propoxur, prothiofos, prothoat, pymetrozine, pyraclofos, pyresmethrin, pyrethrum, pyridaben, pyridathion, pyrimidifen, pyriproxyfen,
quinalphos,
ribavirin,
salithion, sebufos, silafluofen, spinosad, spirodiclofen, sulphotep, sulprofos,
tau-fluvalinate, tebufenozide, tebufenpyrad, tebupirimiphos, teflubenzuron, tefluthrin, temephos, ternivinphos, terbufos, tetrachlorvinphos, tetradifon thetacypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
vamidothion, vaniliprole, *Verticillium lecanii*,
YI 5302
zeta-cypermethrin, zolaprofos
(1R-cis)-[5-(phenylmethyl)-3-furanyl]-methyl-3-[(dihydro-2-oxo-3(2H)-furanylidene)-methyl]-2,2-dimethylcyclopropanecarboxylate,
(3-phenoxyphenyl)-methyl-2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-dimethylethyl)phenyl]-4,5-dihydro-oxazole,
2-(acetyloxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate
4-[4-(4-ethoxyphenyl)-4-methylpentyl)-1-fluoro-2-phenoxy-benzene,
4-chloro-2-(1,1-dimethylethyl)-5-[[2-(2,6-dimethyl-4-phenoxyphenoxy)ethyl]thio]-3(2H)-pyridazinone,
4-chloro-2-(2-chloro-2-methylpropyl)-5-[(6-iodo-3-pyridinyl)methoxy]-3(2H)-pyridazinone,
4-chloro-5-[(6-chloro-3-pyridinyl)methoxy]-2-(3,4-dichlorophenyl)-3(2H)-pyridazinone,
*Bacillus thuringiensis* strain EG-2348,
[2-benzoyl-1-(1,1-dimethylethyl)-hydrazinobenzoic acid,
2,2-dimethyl-3-(2,4-dichlorophenyl)-2-oxo-1-oxaspiro[4.5] dec-3-en-4-yl butanoate,
[3-[(6-chloro-3-pyridinyl)methyl]-2-thiazolidinylidene]-cyanamide,
dihydro-2-(nitromethylene)-2H-1,3-thiazine-3(4H)-carboxaldehyde,
ethyl [2-[[1,6-dihydro-6-oxo-1-(phenylmethyl)-4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]-4,5-dihydro-4-phenyl-1H-pyrazole-1-carboxamide,
N-[(2-chloro-5-thiazolyl)methyl]-N'-methyl-N"-nitroguanidine,
N-methyl-N'-(1-methyl-2-propenyl)-1,2-hydrazinedicarbothioamide,
N-methyl-N'-2-propenyl-1,2-hydrazinedicarbothioamide,
O,O-diethyl [2-(dipropylamino)-2-oxoethyl]-ethylphosphoramidothioate,
N-cyanomethyl-4-trifluoromethyl-nicotinamide,
3,5-dichloro-1-(3,3-dichloro-2-propenyloxy)4-[3-(5-trifluoromethylpyridine-2-yloxy)-propoxy]-benzene.

A mixture with other known active compounds, such as herbicides, or with fertilizers and growth regulators, is also possible.

In addition, the compounds of the formula (I) according to the invention also have very good antimycotic activity. They have a very broad antimycotic activity spectrum in particular against dermatophytes and yeasts, moulds and diphasic fungi, (for example against Candida species, such as *Candida albicans, Candida glabrata*), and *Epidermophyton floccosum*, Aspergillus species, such as *Aspergillus niger* and *Aspergillus fumigatus*, Trichophyton species, such as *Trichophyton mentagrophytes*, Microsporon species such as *Microsporon canis* and *audouinii*. The list of these fungi by no means limits the mycotic spectrum covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application.

For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5000 g/ha.

As already mentioned above, it is possible to treat all plants and their parts with active compounds according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetical engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetical engineering) which are preferably treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasised examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasised are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasised are the increased defence of the plants to fungi, bacteria and viruses by systemic acquired resistance (SAR), systemin, phytoalexins, elicitors and resistance genes and correspondingly expressed proteins and toxins. Traits that are furthermore particularly emphasised are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylurea, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the general formula (I) or the active-compound mixtures according to the invention. The preferred ranges stated above for the active compounds or mixtures also apply to the treatment of these plants. Particular emphasis is given to the treatment of plants with the compounds or mixtures specifically mentioned in the present text.

The invention is illustrated by the examples below.

PREPARATION EXAMPLES

Example 1

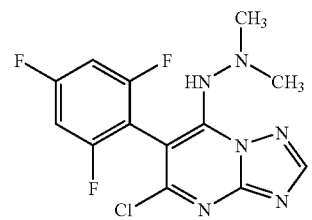

Process (a)

0.234 g of triethylamine is added to a solution of 0.638 g (2 mmol) of 5,7-dichloro-6-(2,4,6-trifluorophenyl)[1,2,4]triazolo[1,5-a]pyrimidine and 0.12 g (2 mmol) of N,N-dimethylhydrazine in 10 ml of dichloromethane. The reaction mixture is stirred at room temperature for 36 hours, then 200 ml of water and 4 ml of 1N hydrochloric acid are added with further stirring. The organic phase is separated off, washed twice with 50 ml of water in each case, dried over sodium sulphate and concentrated under reduced pressure. The residue is triturated with hot diisopropyl ether and filtered off with suction. This gives 238 mg (31% of theory) of 5-chloro-7-(2,2-dimethylhydrazino)-6-(2,4,6-trifluorophenyl)[1,2,4]-triazolo[1,5-a]pyrimidine with a melting point of 165–168° C.

Example 2

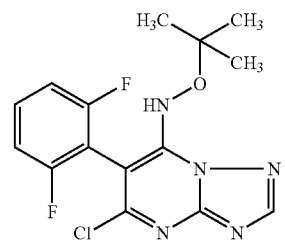

Process (a)

80 mg (0.264 mmol) of 5,7-dichloro-6-(2,6-difluorophenyl)[1,2,4]triazolo[1,5-a]pyrimidine, 33 mg (0.264 mmol) of O-t-butylhydroxylamine hydrochloride and 80 µl of triethylamine are dissolved in 3 ml of dichloromethane and then stirred at 40° C. for one day and at room temperature for one day. The reaction mixture is diluted with 20 ml of dichloromethane, 10 ml of 1N hydrochloric acid are added and the mixture is stirred. The organic phase is separated off, washed with 10 ml of water, dried over sodium sulphate and concentrated under reduced pressure. The residue is stirred with petroleum ether and filtered off with suction. This gives 60 mg (64% of theory) of 7-(tert-butoxyamino)-5-chloro-6-(2,6-difluorophenyl)[1,2,4]triazolo[1,5-a]pyrimidine.

HPLC: logP=2.59

Example 3

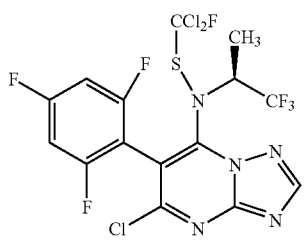

Process (b)

Under argon, first 0.061 g of a 60% strength sodium hydride suspension and then 0.5 g (1.26 mmol) of 5-chloro-N-[(1S)-2,2,2-trifluoro-1-methylethyl]-6-(2,4,6-trifluorophenyl)[1,2,4]triazolo[1,5-a]pyrimidine-7-amine are added to 20 ml of tetrahydrofuran. The mixture is stirred at 0° C. for 30 minutes. A solution of 0.236 g (1.26 mmol) of dichlorofluoromethanesulphenyl chloride in 10 ml of tetrahydrofuran is added dropwise to this mixture, and the mixture is stirred at room temperature for 36 hours. The reaction mixture is then concentrated under reduced pressure. The residue is chromatographed over silica gel using hexane/ethyl acetate (9:1). This gives 0.41 g (59% of theory) of 96.5% pure 5-chloro-7-{{[dichloro(fluoro)methyl]sulphanyl}[(1S)-2,2,2-trifluoro-1-methylethyl]amino}-6-(2,4,6-trifluorophenyl)[1,2,4]triazolo[1,5-a]pyrimidine.

HPLC: logP=4.74

The compounds of the formula (I) named in Table 1 below are also obtained by the methods given above.

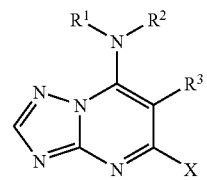

(I)

TABLE 1

| Ex. No. | $R^1$ | $R^2$ | $R^3$ | X | logP* | m.p. (° C.) |
|---|---|---|---|---|---|---|
| 4 | dimethylamino | —H | phenyl | —Cl | | 194–196 |
| 5 | i-propylamino | —H | 2-chlorophenyl | —Cl | | |
| 6 | i-propylamino | —H | 3-chlorophenyl | —Cl | | |
| 7 | n-butylamino | —H | 3-chlorophenyl | —Cl | | |
| 8 | i-butoxy | —H | 2,6-difluorohenyl | —Cl | 2.78 | |
| 9 | #—O—CH₂-(4-phenyl-thiazol-2-yl) | —H | 2,4,6-trifluorophenyl | —Cl | 3.21 | |
| 10 | 4-trifluoromethylbenzyloxy | —H | 2,4,6-trifluorophenyl | —Cl | 3.38 | |
| 11 | 4-trifluoromethoxybenzyloxy | —H | 2,4,6-trifluorophenyl | —Cl | 3.54 | |
| 12 | benzyloxy | —H | 2,4,6-trifluorophenyl | —Cl | 2.92 | |
| 13 | 4-methylbenzyloxy | —H | 2,4,6-trifluorophenyl | —Cl | 3.25 | |
| 14 | cyclopentyloxy | —H | 2,4,6-trifluorophenyl | —Cl | 2.94 | |
| 15 | 2-chloro-5-pyridyloxymethoxy | —H | 2,4,6-trifluorophenyl | —Cl | 2.43 | |
| 16 | —O—CH₃ | —CH₃ | 2,4,6-trifluorophenyl | —Cl | 2.63 | |
| 17 | —NH₂ | —C₂H₅ | 2,4,6-trifluorophenyl | —Cl | 2.27 | 215-18 |
| 18 | methylamino | —CH₃ | 2,4,6-trifluorophenyl | —Cl | 2.33 | 210-11 |
| 19 | —NH—CH₂—CF₃ | —H | 2,4,6-trifluorophenyl | —Cl | 2.47 | oil |
| 20 | —NH₂ | n-propyl | 2,4,6-trifluorophenyl | —Cl | 2.58 | 205-08 |
| 21 | t-butylamino | —H | 2,4,6-trifluorophenyl | —Cl | 2.86 | 235-37 d |
| 22 | —NH₂ | Cyclohexylmethyl | 2,4,6-trifluorophenyl | —Cl | 3.67 | paste |
| 23 | 2-cyanethylemino | —H | 2,4,6-trifluorophenyl | —Cl | 2.03 | 190-91 |
| 24 | allylamino | —H | 2,4,6-trifluorophenyl | —Cl | 2.48 | paste |
| 25 | 1-cyclopropylethylamino | —H | 2,4,6-trifluorophenyl | —Cl | 3.02 | 199-01 |
| 26 | 1-methylethylidenamino | cyclohexylmethyl | 2,4,6-trifluorophenyl | —Cl | 4.5 | oil |
| 27 | 1-methyl-1-cyclohexylamino | —H | 2,4,6-trifluorophenyl | —Cl | 3.68 | paste |
| 28 | —O—CH₃ | —CH₃ | 2,6-difluorophenyl | —Cl | 2.43 | |
| 29 | —NH—CH₂—CF₂—CHF₂ | —H | 2,4,6-trifluorophenyl | —Cl | 2.58 | 203-05 |
| 30 | 1-ethyl-1-propylamino | —H | 2,4,6-trifluorophenyl | —Cl | 3.25 | 130-36 |
| 31 | —O—CH₃ | —H | 2,4,6-trifluorophenyl | —Cl | 2.12 | |
| 32 | —O—CH₃ | —H | 2,6-difluorophenyl | —Cl | 1.92 | |
| 33 | 2-hydroxyethylamino | —H | 2,4,6-trifluorophenyl | —Cl | 1.68 | 215-20 |
| 34 | O-i-propyl | —CH₃ | 2,6-difluorophenyl | —Cl | 3.01 | |
| 35 | cyclohexylamino | —H | 2,4,6-trifluorophenyl | —Cl | 3.28 | paste |
| 36 | i-propylamino | p | 2,6-dichloro-3-fluoro-5-trifluoromethylphenyl | —Cl | 3.51 | oil |
| 37 | i-propylamino | —H | 3-chloro-4-fluorophenyl | —Cl | 2.84 | |
| 38 | —O—CH₃ | i-propyl | | —Cl | 3.11 | |
| 39 | —N—CH₂ | —CH₃ | 2,4,6-trifluorophenyl | —Cl | 2.41 | 165-70 |

TABLE 1-continued

| Ex. No. | R¹ | R² | R³ | X | logP* | m.p. (° C.) |
|---|---|---|---|---|---|---|
| 40 | —O—C₂H₅ | —H | 2,4,6-trifluorophenyl | —Cl | 2.33 | |
| 41 | —O—CH(CH₃)—CH₂—CH₃ | —H | 2,4,6-trifluorophenyl | —Cl | 2.86 | |
| 42 | allyloxy | —H | 2,4,6-trifluorophenyl | —Cl | 2.48 | |
| 43 | t-butoxy | —H | 2,4,6-trifluorophenyl | —Cl | 2.75 | |
| 44 | —NH—CH₂—CH(CH₃)₂ | —H | 2,6-dichloro-3-fluoro-5-trifluoromethylphenyl | —Cl | 3.89 | paste |
| 45 | i-propylamino | —H | 2-chloro-4-fluorophenyl | —Cl | 2.74 | |
| 46 | 3-chlorobenzyloxy | —H | 2,6-difluorophenyl | —Cl | 3.12 | |
| 47 | 4-chlorobenzyloxy | —H | 2,6-difluorophenyl | —Cl | 3.14 | |
| 48 | —O—CH(CH₃)—CH₂—CH₃ | —H | 2,6-difluorophenyl | —Cl | 2.67 | |
| 49 | —O—CH₃—CH₂—CH₂—CH=CH₂ | —H | 2,6-difluorophenyl | —Cl | 2.35 | |
| 50 | allyloxy | —H | 2,6-difluorophenyl | —Cl | 2.28 | |
| 51 | 2-hexahydropyranyloxy | —H | 2,6-difluorophenyl | —Cl | 2.43 | |
| 52 | (2-tetrahydrofuranyl)methylamino | —H | 2,4,6-trifluorophenyl | —Cl | 2.44 | paste |
| 53 | 2-hydroxy-2-methylpropylamino | —H | 2,4,6-trifluorophenyl | —Cl | 2.09 | 165-70 |
| 54 | 2-(N-morpholinyl)ethylamino | —H | 2,4,6-trifluorophenyl | —Cl | 1.14 | 22-30 dec. |
| 55 | cyclopentylamino | —H | 2,4,6-trifluorophenyl | —Cl | 2.98 | 205-07 |
| 56 | i-butoxy | —H | 2-fluorophenyl | —Cl | 2.79 | |
| 57 | —O—C₂H₅ | —H | 2-fluorophenyl | —Cl | 2.13 | |
| 58 | 4-trifluoromethylbenzyloxy | —H | 2-fluorophenyl | —Cl | 3.31 | |
| 59 | 2-chlorobenzyloxy | —H | 2-fluorophenyl | —Cl | 3.06 | |
| 60 | 3-chlorobenzyloxy | —H | 2-fluorophenyl | —Cl | 3.15 | |
| 61 | 4-chlorobenzyloxy | —H | 2-fluorophenyl | —Cl | 3.16 | |
| 62 | 4-fluorobenzyloxy | —H | 2-fluorophenyl | —Cl | 2.82 | |
| 63 | —O—CH(CH₃)—CH₂—CH₃ | —H | 2-fluorophenyl | —Cl | 2.69 | |
| 64 | allyloxy | —H | 2-fluorophenyl | —Cl | 2.27 | |
| 65 | t-butoxy | —H | 2-fluorophenyl | —Cl | 2.58 | |
| 66 | 2-hexahydropyranyloxy | —H | 2-fluorophenyl | —Cl | 2.46 | |
| 67 | —O—CH₃ | —H | 2-fluorophenyl | —Cl | 1.89 | |
| 68 | —O—CH₃ | —CH₃ | 2-fluorophenyl | —Cl | 2.33 | |
| 69 | i-butoxy | —H | pentafluorophenyl | —Cl | 3.42 | |
| 70 | O—C₂H₅ | —H | pentafluorophenyl | —Cl | 2.73 | |
| 71 | 4-chlorobenzyloxy | —H | pentafluorophenyl | —Cl | 3.62 | |
| 72 | 4-fluorobenzyloxy | —H | pentafluorophenyl | —Cl | 3.3 | |
| 73 | —O—CH(CH₃)—CH₂—CH₃ | —H | pentafluorophenyl | —Cl | 3.33 | |
| 74 | allyloxy | —H | pentafluorophenyl | —Cl | 2.89 | |
| 75 | t-butoxy | —H | pentafluorophenyl | —Cl | 3.24 | |
| 76 | 2-hexahydropyranyloxy | —H | pentafluorophenyl | —Cl | 3.04 | |
| 77 | —O—CH₃ | —CH₃ | pentafluorophenyl | —Cl | 3.06 | |
| 78 | 3-methylbutylamino | —H | 2,4,6-trifluorophenyl | —Cl | 3.25 | 158-60 |
| 79 | i-butoxy | —H | 2,4,6-trifluorophenyl | —Cl | 3 | |
| 80 | 3,5-dichlorobenzyloxy | —H | 2,4,6-trifluorophenyl | —Cl | 3.73 | |
| 81 | 2-chlorobenzyloxy | —H | 2,4,6-trifluorophenyl | —Cl | 3.22 | |
| 82 | 3-chlorobenzyloxy | —H | 2,4,6-trifluorophenyl | —Cl | 3.27 | |
| 83 | 4-fluorobenzyloxy | —H | 2,4,6-trifluorophenyl | —Cl | 2.99 | |
| 84 | 3-trifluoromethylbenzyloxy | —H | 2,4,6-trifluorophenyl | —Cl | 3.39 | |
| 85 | -n-butoxy | —H | 2,4,6-trifluorophenyl | —Cl | 3.01 | |
| 86 | 2,6-dichlorobenzyloxy | —H | 2,4,6-trifluorophenyl | —Cl | 3.32 | |
| 87 | dimethylamino | —H | 2-fluorophenyl | —Cl | 2.26 | |
| 88 | —NH—CH₃ | —CH₃ | 2-fluorophenyl | —Cl | 2.13 | |
| 89 | ethylamino | —H | 2-fluorophenyl | —Cl | 2.06 | |
| 90 | n-butylamino | —H | 2-fluorophenyl | —Cl | 2.77 | |
| 91 | —NH—CH₂—CH₂—CH₂— | —H | 2-fluorophenyl | —Cl | 2.46 | |
| 92 | —NH—CH₂—CH₂— | —H | 2-fluorophenyl | —Cl | 2.31 | |
| 93 | —N(CH₃)—COOCH₃ | —H | 2-fluorophenyl | —Cl | 1.8 | |
| 94 | 2-cyanethylamino | —H | 2-fluorophenyl | —Cl | 1.82 | |
| 95 | benzyloxy | —H | 2-fluorophenyl | —Cl | 2.83 | |
| 96 | 3,5-dichlorobenzyloxy | —H | 2-fluorophenyl | —Cl | 3.69 | |
| 97 | 2,4-dichlorobenzyloxy | —H | 2-fluorophenyl | —Cl | 3.6 | |
| 98 | O-i-propyl | —H | 2-fluorophenyl | —Cl | 2.42 | |
| 99 | 3-trifluoromethylbenzyloxy | —H | 2-fluorophenyl | —Cl | 3.34 | |
| 100 | -n-butoxy | —H | 2-fluorophenyl | —Cl | 2.85 | |
| 101 | 2,6-dichlorobenzyloxy | —h | 2-fluorophenyl | —Cl | 3.3 | |
| 102 | —O—C₂H₅ | —H | 2,6-difluorophenyl | —Cl | 2.18 | |
| 103 | benzyloxy | —H | 2,6-difluorophenyl | —Cl | 2.8 | |
| 104 | 3,5-dichlorobenzyloxy | —H | 2,6-difluorophenyl | —Cl | 3.63 | |
| 105 | 4-trifluoromethylbenzyloxy | —H | 2,6-difluorophenyl | —Cl | 3.32 | |
| 106 | 2-chlorobenzyloxy | —H | 2,6-difluorophenyl | —Cl | 3.07 | |
| 107 | 4-fluorobenzyloxy | —H | 2,6-difluorophenyl | —Cl | 2.86 | |
| 108 | 3-trifluoromethylbenzyloxy | —H | 2,6-difluorophenyl | —Cl | 3.3 | |
| 109 | n-butoxy | —H | 2,6-difluorophenyl | —Cl | 2.83 | |
| 110 | 2,6-dichlorobenzyloxy | —H | 2,6-difluorophenyl | —Cl | 3.2 | |
| 111 | —O—CH(CH₂)—CH₃—CH₂ | —CH₃ | 2,4,6-trifluorophenyl | —Cl | | |
| 112 | benzyloxy | —H | pentafluorophenyl | —Cl | 3.37 | |
| 113 | 3,5-dichlorobenzyloxy | —H | pentafluorophenyl | —Cl | 4.07 | |
| 114 | 2,4-dichlorobenzyloxy | —H | pentafluorophenyl | —Cl | 4.02 | |

TABLE 1-continued

| Ex. No. | R¹ | R² | R³ | X | logP* | m.p. (° C.) |
|---|---|---|---|---|---|---|
| 115 | 4-trifluoromethylbenzyloxy | —H | pentafluorophenyl | —Cl | 3.77 | |
| 116 | 2-chlorobenzyloxy | —H | pentafluorophenyl | —Cl | 3.58 | |
| 117 | 3-chlorobenzyloxy | —H | pentafluorophenyl | —Cl | 3.64 | |
| 118 | 3-trifluoromethylbenzyloxy | —H | pentafluorophenyl | —Cl | 3.72 | |
| 119 | -n-butoxy | —H | pentafluorophenyl | —Cl | 3.49 | |
| 120 | 2,6-dichlorobenzyloxy | —H | pentafluorophenyl | —Cl | 3.65 | |
| 121 | —O—CH₃ | —H | pentafluorophenyl | —Cl | 2.53 | |
| 122 | O-i-propyl | —H | pentafluorophenyl | —Cl | 3.04 | |
| 123 | —OH | —CH₃ | 2,4,6-trifluorophenyl | —Cl | 1.99 | |
| 124 | —OH | —CH₃ | 2,6-difluorophenyl | —Cl | 2.19 | |
| 125 | —NH₂ | cyclohexyl | 2,4,6-trifluorophenyl | —Cl | 3.33 | paste |
| 126 | —NH₂ | i-butyl | 2,6-dichloro-3-fluoro-5-trifluoromethylphenyl | —Cl | 2.58 | paste |
| 127 | —NH₂ | (2-tetrahydrofuryl)-methyl | 2,4,6-trifluorophenyl | —Cl | 2.55 | 154–55 |
| 128 | —NH₂ | 2-methoxyethyl | 2,4,6-trifluorophenyl | —Cl | 2.26 | 141-43 |
| 129 | —NH₂ | 2-(N-morpholinyl)ethyl | 2,4,6-trifluorophenyl | —Cl | 1.1 | paste |
| 130 | —NH₂ | cyclopentyl | 2,4,6-trifluorophenyl | —Cl | 3.07 | 189-82 |
| 131 | —NH₂ | i-butyl | 2,4,6-trifluorophenyl | —Cl | 2.91 | 209-11 |
| 132 | —NH₂ | n-butyl | 2,4,6-trifluorophenyl | —Cl | 2.96 | 167-68 |
| 133 | —NH₂ | -i-propyl | 2,4,6-trifluorophenyl | —Cl | 2.62 | 204-05 |
| 134 | —NH₂ | -i-propyl | 2-fluoro-4-trifluoromethylphenyl | —Cl | 3.08 | paste |
| 135 | —NH₂ | i-butyl | 2-fluoro-4-trifluoromethylphenyl | —Cl | 3.43 | 165-72 |
| 136 | —NH₂ | i-butyl | 2,6-dichloro-4-trifluoromethylphenyl | —Cl | 3.85 | 211-13 |
| 137 | —NH₂ | i-butyl | 2,5-bis-(trifluoromethyl)-phenyl | —Cl | 3.57 | 211-14 |
| 138 | —NH₂ | i-butyl | 2-chloro-6-fluorophenyl | —Cl | 2.94 | 158-60 |
| 139 | —NH₂ | 2-butyl | 2,4,6-trifluorophenyl | —Cl | 2.93 | 175-76 |
| 140 | —NH₂ | i-butyl | 2-chloro-5-trifluoromethylphenyl | —Cl | 3.51 | 178-81 |
| 141 | —NH₂ | cycloheptyl | 2,4,6-trilfuorophenyl | —Cl | 3.66 | 201-03 |
| 142 | —NH₂ | propargyl | 2,4,6-trifluorophenyl | —Cl | 2.22 | 177-80 |
| 143 | —OH | —CH₃ | 2-tolyl | —Cl | | |
| 144 | —NH₂ | 2-butyl | 2-chloro-3-trifluoromethylphenyl | —Cl | 3.44 | paste |
| 145 | sec-butylamino | —H | 2-chloro-3-trifluoromethylphenyl | —Cl | 3.37 | paste |
| 146 | —NH₂ | 2-butyl | 2-chloro-5-trifluoromethylphenyl | —Cl | 3.99 | paste |
| 147 | sec-butylamino | —H | 2-chloro-5-trifluoromethylphenyl | —Cl | 3.95 | paste |
| 148 | —NH₂ | 2-butyl | 2-chloro-5-trifluoromethylphenyl | —Cl | 3.53 | paste |
| 149 | sec-butylamino | —H | 2-chloro-5-trifluoromethylphenyl | —Cl | 3.47 | paste |
| 150 | —NH₂ | 2-butyl | 2,2-difluoro-1,3-benzodioxol-4-yl | —Cl | 3.27 | |
| 151 | sec-butylamino | —H | 2,2-difluoro-1,3-benzodioxol-4-yl | —Cl | 3.21 | |
| 152 | O—CH₃ | i-butyl | 2,4,6-trifluorophenyl | —Cl | 3.78 | |
| 153 | —NH₃⁺Cl— | i-butyl | 2,4,6-trifluorophenyl | —Cl | 2.88 | 145-8 |
| 154 | sec-butylamino | —H | 2,6-dichlorophenyl | —Cl | 3.14 | 189-91 |
| 155 | —NH₂ | i-butyl | 2,6-dichlorophenyl | —Cl | 3.17 | 164-6 |
| 156 | —NH—CH₂—CH(CH₃)₂ | —H | 2,6-dichlorophenyl | —Cl | 3.18 | paste |
| 157 | acetylamino | i-butyl | 2,4,6-trifluorophenyl | —Cl | 2.25 | 184-6 |
| 158 | 1-methylethylideneamino | i-butyl | 2,4,6-trifluorophenyl | —Cl | 3.63 | 142-4 |
| 159 | NH₂ | cyclopropyl-methyl | 2,4,6-trifluorophenyl | —Cl | 2.66 | 158-60 |
| 160 | cyclopentylamino | —H | 2,6-dichlorophenyl | —Cl | 3.21 | 225-7 dec. |
| 161 | —NH₂ | cyclopentyl | 2,6-dichlorophenyl | —Cl | 3.37 | paste |
| 162 | —NH₂ | cyclopropyl-methyl | 2-chloro-6-fluorophenyl | —Cl | 2.63 | 143.5 |
| 163 | —NH₂ | i-butyl | 2-chloro-3-trifluoromethylphenyl | —Cl | 3.45 | paste |
| 164 | —NH₂ | cyclopropyl-methyl | 2,6-dichlorophenyl | —Cl | 2.8 | 178-9 |
| 165 | N=C(CH₃)—CF₃ | —H | 2,4,6-trifluorophenyl | —Cl | 3.07 | paste |
| 166 | —NH₂ | (2,2-dichlorocyclopropyl)-methyl | 2,4,6-trifluorophenyl | —Cl | 3.11 | |

TABLE 1-continued

| Ex. No. | R¹ | R² | R³ | X | logP* | m.p. (° C.) |
|---|---|---|---|---|---|---|
| 167 | —N=CH—CH₃ | (2,2-dichloro-cyclopropyl)-methyl | 2,4,6-trifluorophenyl | —Cl | 3.72 | |
| 168 | —NH—CO—O—C₂H₅ | i-butyl | 2,4,6-trifluorophenyl | —Cl | 2.99 | |
| 169 | —NH₂ | cyclobutyl-methyl | 2,4,6-trifluorophenyl | —Cl | 3.06 | |
| 170 | —NH₂ | i-butyl | 2,6-difluorophenyl | —Cl | 2.72 | 137-40 |
| 171 | —NH₂ | (2,2-dichloro-cyclopropyl)-methyl | 2-chloro-6-fluoro-phenyl | —Cl | 3.11 | |
| 172 | —NH₂ | i-butyl | 2-chloro-4-fluorophenyl | —Cl | 3.15 | |
| 173 | —NH₂ | cyclobutylmethyl | 2-chloro-6-fluorophenyl | —Cl | 3.07 | | denotes the point of attachment

*) The logP values were determined in accordance with EEC directive 79/831 Annex V. A8 by HPLC (gradient method, acetonitrile/0.1% aqueous phosphoric acid)

Example 174

Process (c), first stage:

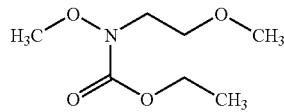
(VIII-1)

1 000 mg of ethyl N-methoxycarbamate are introduced into 10.0 ml of dimethylformamide and, in portions, 403 mg of sodium hydride are added, the temperature being adjusted to 30° C. by cooling. The reaction mixture is stirred at 30° C. for 2 hours and then 3 500 mg of 2-bromoethyl methyl ether are added. The reaction mixture is stirred at 20° C. to 25° C. for 18 hours and then stirred into 20 ml of water. The reaction mixture obtained is concentrated to dryness under reduced pressure and extracted with four times 30 ml of dichloromethane. The organic extracts are dried over sodium sulphate, filtered and concentrated to dryness under reduced pressure.

This gives 1 200 mg of ethyl (N-methoxy-N-methoxyethyl)carbamate (purity 77.6%, yield 62.6%).

Process (c), second stage:

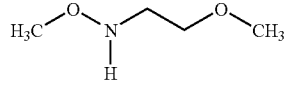
(III-1)

200 mg of ethyl (N-methoxy-N-methoxyethyl)carbamate are introduced into 4.0 ml of aqueous ethanol (59%), 240.6 mg of potassium hydroxide are added and the mixture is stirred at 40° C. for 18 hours. The reaction mixture is then stirred into 50 ml of water and extracted with three times 20 ml of diethyl ether and with three times 20 ml of dichloromethane. The combined organic phases are washed twice with 20 ml portions of water, dried and concentrated to a volume of 20 ml under reduced pressure at 20° C.

With ice cooling, 2 ml of hydrochloric acid are added to the resulting solution, which is stirred at room temperature for 1 hour and concentrated to dryness under reduced pressure at 20° C.

The product obtained is digested with three times 15 ml of methanol and then concentrated to dryness under reduced pressure at 20° C.

This gives 140 mg of N-methoxy-N-methoxyethylamine hydrochloride (yield 87.6%).

Example 175

Process (d), first stage:

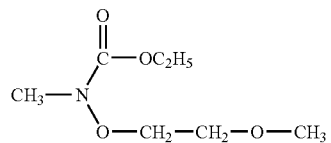
(X-1)

A mixture of 1 000 mg of ethyl N-hydroxy-N-methylcarbamate, 1 166 mg of 2-bromoethyl methyl ether and 10 ml of ethanol is heated to reflux temperature with stirring and then a solution of 493 mg of potassium hydroxide in 5 ml of ethanol is added dropwise. The reaction mixture is boiled under reflux for 10 hours and then worked up by filtering the reaction mixture and concentrating the filtrate under reduced pressure. The residue which remains is admixed with a mixture of water and ethyl acetate. The organic phase is separated off and washed with saturated aqueous ammonium chloride solution and then with water. The organic phase is subsequently dried over sodium sulphate and concentrated under reduced pressure. This gives 0.7 g of a product which according to the gas chromatogram consists of 83% ethyl (N-methyl-N-methoxyethoxy)-carbamate. The yield is calculated accordingly to be 39% of theory.

Process (d), second stage:

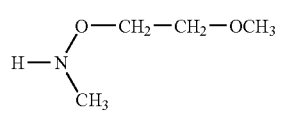
(III-2)

A mixture of 200 mg of ethyl (N-methyl-N-methoxyethoxy)-carbamate, 4 ml of ethanol and 4 ml of water is admixed with 240.6 mg of powdered potassium hydroxide and stirred at 40° C. for 2 hours. The reaction mixture is subsequently stirred into 50 ml of water then extracted with three times 20 ml of diethyl ether and subsequently with three times 20 ml of methylene chloride. The combined organic phases are washed twice with 20 ml portions of water, dried over sodium sulphate and concentrated to a volume of 20 ml under reduced pressure at room temperature. With ice cooling, 1 ml of ethereal hydrochloric acid is added to the solution obtained. The crystals which deposit are filtered off and dried. This gives 190 mg of N-methyl-N-methoxyethoxyamine hydrochloride.

Example 176

Process (e), first stage:

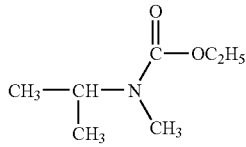
(XIII-1)

475 mg of sodium hydride are added with stirring at room temperature to a mixture of 2 000 mg of ethyl N-(2,2,2-trifluoro-1-methyl-ethyl)-carbamate and 20 ml of tetrahydrofuran. A solution of 4 600 mg of iodomethane in 10 ml of tetrahydrofuran is then added dropwise with stirring at room temperature. The reaction mixture is stirred at 50° C. for 16 hours and then water is added. It is extracted with three times 20 ml of methylene chloride and the combined organic phases are dried over sodium sulphate and concentrated under reduced pressure. This gives 1 000 mg of a product which according to the current gas chromatogram consists of 75% ethyl N-(2,2,2-trifluoro-1-methyl-ethyl)-N-methyl-carbamate. The yield is calculated accordingly to be 34.86%.

Process (e), second stage:

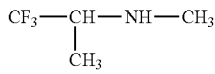
(III-3)

A mixture of 1 000 mg of ethyl N-(2,2,2-trifluoro-1-methyl-ethyl)-N-methyl-carbamate, 20 ml of ethanol and 20 ml of water is admixed with 1 070 mg of powdered potassium hydroxide and stirred at 40° C. for 66 hours. The reaction mixture is then diluted with water and extracted with three times 20 ml of a mixture consisting of equal parts of methylene chloride and diethyl ether. The combined organic phases are dried over sodium sulphate and then concentrated under slightly reduced pressure at room temperature. With ice cooling, ethereal hydrochloric acid is added to the solution obtained, which is stirred at room temperature for 60 hours. Concentration under reduced pressure gives 280 mg of N-(2,2,2-trifluoro-1-methyl-ethyl)-N-methylamine hydrochloride. The yield is calculated accordingly to be 34% of theory.

Example 177

Process (f):

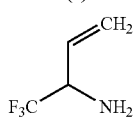
(III-4)

600 mg of benzyl N-(1-trifluoromethyl-2-propene)-carbamate are heated under reflux in 8.0 ml of 16% strength hydrochloric acid for 1.5 hours. After the mixture has been cooled to 20° C. it is extracted with twice 20 ml of diethyl ether.

The aqueous phase which remains is concentrated to dryness under reduced pressure and admixed with three times 10 ml of methanol. Following removal of the methanol under reduced pressure, 310 mg of (1-trifluoromethyl-prop-2-ene)-amine hydrochloride are isolated. The yield is calculated accordingly to be 82.9% of theory.

In accordance with the methods indicated above it is also possible to prepare the carbamates indicated in the tables below.

TABLE 2

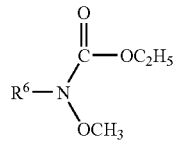
(VIII)

| Example No. | Comp. No. | $R^6$ | logP |
|---|---|---|---|
| 178 | VIII-2 | CH$_3$—CH—CH$_2$—<br>          \|<br>          CH$_3$ | 2.38 |
| 179 | VIII-3 | CH$_2$=C—CH$_2$—<br>      \|<br>      CH$_3$ | 2.06 |

TABLE 3

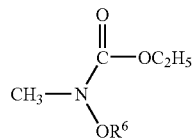
(X)

| Example No. | Comp. No. | $R^6$ | Physical constants |
|---|---|---|---|
| 180 | X-2 | CH$_2$=C—CH$_2$—<br>      \|<br>      CH$_3$ | |

TABLE 4

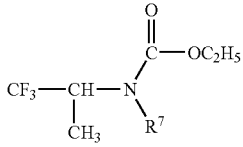
(XIII)

| Example No. | Comp. No. | $R^7$ | Physical constants |
|---|---|---|---|
| 181 | XIII-2 | —C$_2$H$_5$ | $^1$H-NMR(400 MHz, CD$_3$CN):<br>δ(ppm)=1.13(t, C$\underline{H}_3$CH$_2$N), 1.21 (t, C$\underline{H}_3$CHCF$_3$), 1.23(t, C$\underline{H}_3$CH$_2$O), 3.20(m, C$\underline{H}_2$N, C$\underline{H}$CF$_3$), 4.1(q, CH$_3$C$\underline{H}_2$O). |

In accordance with the methods indicated above it is also possible to prepare the amines set out in the table below.

TABLE 5

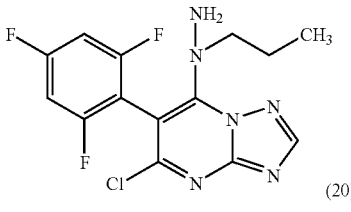

| Example No. | Comp. No. | R¹ | R² | Physical constants |
|---|---|---|---|---|
| 182 | III-5 | CH₃—CH(CH₃)—CH₂— | —OCH₃ | ¹H-NMR(400 MHz, CD₃CN): δ(ppm)=1.03(d, C$\underline{H}$₃)₂CH), 3.06(d, CH₂), 3.28(b, (CH₃)₂CH), 4.01(s, OCH₃) |
| 183 | III-6 | CH₂=C(CH₃)—CH₂— | —OCH₃ | ¹H-NMR(400 MHz, DMSO): δ(ppm)=1.76(s, C$\underline{H}$₃(CCH₂)CH₂), 3.29(b, NH, CH₃(CCH₂)C$\underline{H}$₂, OCH₃), 7.89, 5.02(2s, CH₃(CC$\underline{H}$₂)CH₂). |
| 184 | III-7 | CH₂=C(CH₃)—CH₂— | | |
| 185 | III-8 | CF₃—CH(CH₃)— | —C₂H₅ | ¹H-NMR(400 MHz, DMSO): δ(ppm)=1.06(m, C$\underline{H}$₃CH₂N, C$\underline{H}$₃CHCF₃, 3.20(m, C$\underline{H}$₂N), 4.1(m, C$\underline{H}$CF₃). |

The amines set out in examples 182–185 were each isolated and characterized in the form of their hydrochlorides.

EXAMPLES

Example A

| Fusarium nivale (var. majus) test (wheat)/protective | |
|---|---|
| Solvent: | 25 parts by weight of N,N-dimethylacetamide |
| Emulsifier: | 0.6 part by weight of alkylaryl polyglycol ether |

To produce a suitable preparation of active compound, one part by weight of active compound is mixed with the stated amounts of solvent and emulsifier, and the concentrate is diluted with water to the desired concentration.

To test for protective activity, young plants are sprayed with the active compound preparation at the application rate indicated. After the spray coating has dried on, the plants are sprayed with a conidia suspension of *Fusarium nivale* (var. majus).

The plants are placed in a greenhouse under transparent incubation hoods at a temperature of about 15° C. and a relative humidity of about 100%.

Evaluation is made 4 days following inoculation. 0% denotes an efficacy corresponding to that of the control, whereas an efficacy of 100% means that no infestation is observed.

Active compounds, their application rates, and experimental results are indicated in the following table.

TABLE A

Fusarium nivale (var. majus) test (wheat)/protective

| Active compound | Application rate of active compound in g/ha | Efficacy in % |
|---|---|---|
| (inventive) 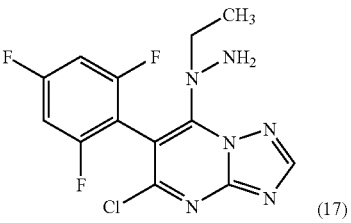 (20) | 500 | 80 |
| (17) | 500 | 80 |
| (18) | 500 | 93 |

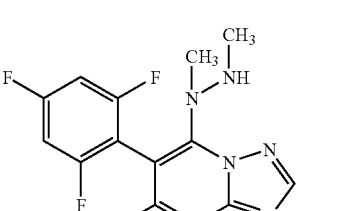

Example B

| Venturia test (apple)/protective | |
|---|---|
| Solvent: | 24.5 parts by weight of acetone |
|  | 24.5 parts by weight of N,N-dimethylacetamide |
| Emulsifier: | 1.0 part by weight of alkylaryl polyglycol ether |

To produce a suitable preparation of active compound, one part by weight of active compound is mixed with the stated amounts of solvent and emulsifier, and the concentrate is diluted with water to the desired concentration.

To test for protective activity, young plants are sprayed with the active compound preparation at the application rate indicated. After the spray coating has dried on, the plants are inoculated with an aqueous conidia suspension of the apple scab causative organism, *Venturia inaequalis*, and then remain in an incubation cabin for 1 day at about 20° C. and 100% relative humidity.

The plants are placed in a greenhouse at a temperature of about 15° C. and a relative humidity of about 90%.

Evaluation is made 10 days following inoculation. 0% denotes an efficacy corresponding to that of the control, whereas an efficacy of 100% means that no infestation is observed.

Active compounds, their application rates, and experimental results are indicated in the following table.

TABLE B

| | Venturia test (apple)/protective | |
|---|---|---|
| Active compound | Application rate of active compound in g/ha | Efficacy in % |
| (inventive) 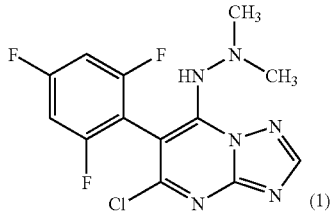 (1) | 100 | 94 |

Example C

| Alternaria test (tomato)/protective | |
|---|---|
| Solvent: | 49 parts by weight of N,N-dimethylformamide |
| Emulsifier: | 1 part by weight of alkylaryl polyglycol ether |

To produce an appropriate preparation of active compound, 1 part by weight of active compound is mixed with the stated amounts of solvent and emulsifier, and the concentrate is diluted with water to the desired concentration.

To test for protective activity, young tomato plants are sprayed with the active compound preparation at the application rate indicated. One day after treatment, the plants are inoculated with a spore suspension of *Alternaria solani* and then stand at 100% relative humidity and 20° C. for 24 h. The plants subsequently stand at 96% relative humidity and a temperature of 20° C.

Evaluation is made 7 days after inoculation. 0% denotes an efficacy corresponding to that of the control while an efficacy of 100% means that no infestation is observed.

Active compounds, their application rates, and experimental results are indicated in the following table.

TABLE C

| | Alternaria test (tomato)/protective | |
|---|---|---|
| Active compound | Application rate of active compound in g/ha | Efficacy in % |
| (inventive) 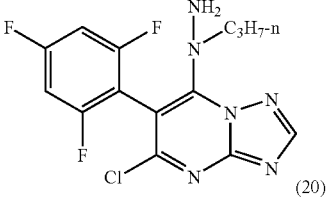 (20) | 750 | 94 |
| 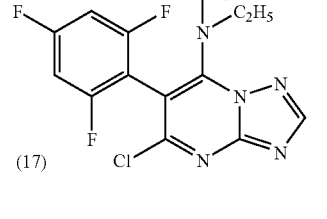 (17) | 750 | 89 |
| 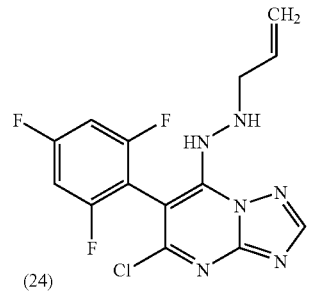 (24) | 750 | 94 |
| Inventive 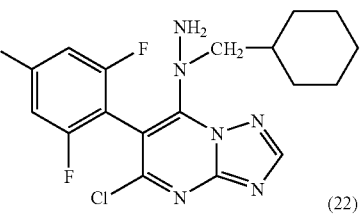 (22) | 750 | 94 |

TABLE C-continued

Alternaria test (tomato)/protective

| Active compound | Application rate of active compound in g/ha | Efficacy in % |
|---|---|---|
| 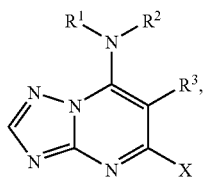 (21) | 750 | 94 |

The invention claimed is:

1. A triazolopyrimidine of formula (I)

(I)

in which
R¹ represents hydroxyl, amino, alkylcarbonylamino, N-alkyl-N-alkoxycarbonyl-amino, or alkoxycarbonylamino; represents optionally substituted alkoxy, optionally substituted alkenyloxy, optionally substituted alkynyloxy, optionally substituted cycloalkyloxy, optionally substituted alkylamino, optionally substituted dialkylamino, optionally substituted alkenylamino, optionally substituted alkynylamino, cyclopropylamino, cyclobutylamino, cyclopentyl-amino, cyclohexylamino, optionally substituted N-cycloalkyl-N-alkylamino, optionally substituted alkylideneamino, or optionally substituted heterocyclyloxy; or represents a radical of the formula -S-R4, in which R4 represents optionally substituted alkyl, optionally substituted alkenyl, optionally substituted alkynyl, or optionally substituted cycloalkyl,
R² represents hydrogen, optionally substituted alkyl, optionally substituted alkenyl, optionally substituted alkynyl, or optionally substituted cycloalkyl,
R³ represents optionally substituted aryl, and
X represents halogen,
with the proviso that if R¹ represents amino, then the compound of formula (I) is optionally an acid addition salt thereof.

2. A triazolopyrimidine according to claim 1 wherein
R¹ represents hydroxyl, amino, alkylcarbonylamino having 1 to 6 carbon atoms in the alkyl group, N-alkyl-N-alkoxycarbonyl-amino having 1 to 6 carbon atoms in the alkyl group and 1 to 6 carbon atoms in the alkoxy group, or alkoxy-carbonylamino having 1 to 6 carbon atoms in the alkoxy group; represents alkoxy having 1 to 7 carbon atoms that is optionally substituted by halogen, cycloalkyl, cyano, phenyl, phenoxy, heterocyclyl, and/or heterocyclyloxy; represents alkenyloxy having 2 to 6 carbon atoms that is optionally substituted by halogen, cycloalkyl, cyano, phenyl, and/or heterocyclyl; represents alkynyloxy having 2 to 6 carbon atoms that is optionally substituted by halogen, cycloalkyl, cyano, phenyl, and/or heterocyclyl; represents cyclo-alkyloxy having 3 to 7 carbon atoms which is optionally substituted by halogen, cycloalkyl, cyano, phenyl, and/or heterocyclyl; represents alkylamino having 1 to 7 carbon atoms that is optionally substituted by halogen, cycloalkyl, cyano, hydroxyl, phenyl, and/or heterocyclyl; represents dialkyl-amino having 1 to 7 carbon atoms in each of the alkyl radicals, each of which is optionally substituted by halogen, cycloalkyl, cyano, phenyl, and/or heterocyclyl; represents alkenylamino having 2 to 6 carbon atoms that is optionally substituted by halogen, cycloalkyl, cyano, phenyl, and/or heterocyclyl; represents alkynylamino having 2 to 6 carbon atoms that is optionally substituted by halogen, cycloalkyl, cyano, phenyl, and/or heterocyclyl; represents cyclopropylamino, cyclobutylamino, cyclopentyl amino, cyclohexylamino; represents N-cycloalkyl-N-alkyl-amino having 3 to 7 carbon atoms in the cycloalkyl moiety and 1 to 7 carbon atoms in the alkyl moiety and being optionally substituted by halogen, cycloalkyl, cyano, phenyl, and/or heterocyclyl; represents alkylideneamino having 1 to 6 carbon atoms that is optionally substituted by halogen, cycloalkyl, cyano, phenyl, and/or heterocyclyl; represents optionally substituted heterocyclyloxy having 5 or 6 ring members and 1 or 2 heteroatoms in the heterocycle; or represents SR4 in which
R⁴ represents alkyl having 1 to 6 carbon atoms that is optionally substituted by halogen, cycloalkyl, cyano, phenyl, and/or heterocyclyl;
represents alkenyl having 2 to 6 carbon atoms that is optionally substituted by halogen, cycloalkyl, cyano, phenyl, and/or heterocyclyl;
represents alkynyl having 2 to 6 carbon atoms that is optionally substituted by halogen, cycloalkyl, cyano, phenyl, and/or heterocyclyl;
or represents cycloalkyl having 3 to 7 carbon atoms that is optionally substituted by halogen, cycloalkyl, cyano, phenyl, and/or heterocyclyl,
with the provisos that
(1) each heterocyclyl radical is optionally mono- to trisubstituted by identical or different substituents selected from the group consisting of halogen, alkyl having 1 to 4 carbon atoms, halogenoalkyl having 1 or 2 carbon atoms and 1 to 5 halogen atoms, alkoxy having 1 to 4 carbon atoms, alkylthio having 1 to 4 carbon atoms, halogenoalkoxy having 1 or 2 carbon atoms and 1 to 5 halogen atoms, halogenoalkylthio having 1 or 2 carbon atoms and 1 to 5 halogen atoms, and phenyl, and
(2) each phenyl radical is optionally mono- to trisubstituted by identical or different substituents selected from the group consisting of halogen, cyano, nitro, amino, hydroxyl, formyl, carboxyl, carbamoyl, and thiocarbamoyl; represents straight-chain or branched alkyl, alkoxy, alkylthio, alkylsulphinyl or alkylsulphonyl, each having 1 to 6 carbon atoms; straight-chain or branched alkenyl or alkenyloxy, each having 2 to 6 carbon atoms; straight-chain or branched halogenoalkyl, halogenoalkoxy, halogenoalkylthio, halogenoalkylsulphinyl, or halogenoalkylsulphonyl, each having 1 to 6 carbon atoms and 1 to 13 identical or different halogen atoms; straight-chain or branched halogenoalkenyl or halogenoalkenyloxy, each having 2 to 6 carbon atoms and 1 to 13 identical or different halogen atoms; straight-chain or branched alkylamino, dialkylamino, alkylcarbonyl, alkylcarbonyloxy, alkoxycarbonyl, alkylsulphonyloxy, hydroximinoalkyl, or alkoximino alkyl, each having 1 to 6 carbon atoms in the individual alkyl moieties; cycloalkyl having 3 to 6 carbon atoms; or is optionally monosubstituted by alkylene having 3 or 4 carbon atoms or dioxyalkylene having 1 or 2 carbon atoms, each of which is doubly attached in the ortho position and each of which is optionally mono- to tetrasubstituted by identical or different substituents selected from the group consisting of halogen, alkyl having 1 to 4 carbon atoms, and halogenoalkyl having 1 to 4 carbon atoms and 1 to 9 identical or different halogen atoms, $R^2$ represents hydrogen; represents alkyl having 1 to 6 carbon atoms that is optionally substituted by halogen, alkoxy having 1 or 2 carbon atoms, alkylthio having 1 or 2 carbon atoms, oxo, hydroximino, alkoximino having 1 or 2 carbon atoms, cycloalkyl having 3 to 7 carbon atoms, cycloalkyl having 3 to 6 carbon atoms that is substituted by halogen, and/or heterocyclyl; represents alkenyl having 2 to 4 carbon atoms that is optionally substituted by halogen and/or cycloalkyl having 3 to 6 carbon atoms; represents alkynyl having 2 to 4 carbon atoms that is optionally substituted by halogen and/or cycloalkyl having 3 to 6 carbon atoms; or represents cycloalkyl having 3 to 8 carbon atoms that is optionally substituted by halogen and/or cycloalkyl having 3 to 6 carbon atoms, $R^3$ represents phenyl that is optionally mono- to pentasubstituted by identical or different substituents selected from the group consisting of halogen, cyano, nitro, amino, hydroxyl, formyl, carboxyl, carbamoyl, thiocarbamoyl; straight-chain or branched alkyl, alkoxy, alkylthio, alkylsulphinyl, or alkylsulphonyl, each having 1 to 6 carbon atoms; straight-chain or branched alkenyl or alkenyloxy, each having 2 to 6 carbon atoms; straight-chain or branched halogenoalkyl, halogenoalkoxy, halogenoalkylthio, halogenoalkylsulphinyl, or halogenoalkylsulphonyl, each having 1 to 6 carbon atoms and 1 to 13 identical or different halogen atoms; straight-chain or branched halogeno-alkenyl, or halogenoalkenyloxy, each having 2 to 6 carbon atoms and 1 to 13 identical or different halogen atoms; straight-chain or branched alkylamino, dialkylamino, alkylcarbonyl, alkylcarbonyloxy, alkoxycarbonyl, alkylsulphonyloxy, hydroximinoalkyl, or alkoximinoalkyl, each having 1 to 6 carbon atoms in the individual alkyl moieties; cycloalkyl having 3 to 6 carbon atoms; or is optionally monosubstituted by alkylene having 3 or 4 carbon atoms or dioxyalkylene having 1 or 2 carbon atoms, each of which is doubly attached in the ortho position and each of which is optionally mono- to tetrasubstituted by identical or different substituents selected from the group consisting of halogen, alkyl having 1 to 4 carbon atoms, and halogenoalkyl having 1 to 4 carbon atoms and 1 to 9 identical or different halogen atoms, and X represents fluorine, chlorine or bromine.

3. A process for preparing a triazolopyrimidine of formula (I) according to claim 1 comprising (a) reacting a dihalogeno-triazolopyrimidine of formula (II)

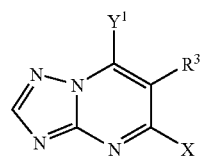

(II)

in which $R^3$ and X have the meanings given for formula (I) in claim 1, and $Y^1$ represents halogen, with an amine of formula (III)

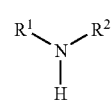

(III)

in which $R^1$ and $R^2$ have the meanings given for formula (I) in claim 1, optionally in the presence of a diluent and optionally in the presence of an acid acceptor, or (b) reacting a triazolopyrimidine of formula (IV)

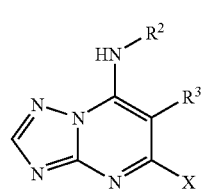

(IV)

in which $R^2$, $R^3$, and X have the meanings given for formula (I) in claim 1, with a sulphenyl halide of formula (V)

(V)

in which $R^4$ has the meanings given for formula (I) in claim 1, and $Y^2$ represents halogen, optionally in the presence of a diluent and optionally in the presence of an acid acceptor.

4. A process for preparing an acid addition salt of a triazolopyrimidine of formula (I) according to claim 1 in which $R^1$ represents amino comprising adding an acid to the compound of formula (I) in which $R^1$ represents amino.

5. A composition for controlling unwanted microorganisms comprising one or more triazolopyrimidines of formula (I) according to claim 1 or an acid addition salt thereof and one or more extenders and/or surfactants.

6. A method of controlling unwanted fungi comprising applying an effective amount of one or more triazolopyrimidines of formula (I) according to claim 1 or an acid addition salt thereof to the unwanted fungi and/or their habitat.

7. A process for preparing a composition for controlling unwanted microorganisms comprising mixing a triazolopyrimidine of formula (I) according to claim 1 or an acid addition salt thereof with one or more extenders and/or surfactants.

* * * * *